April 25, 1972 W. H. DANIEL Plant Pat. 3,135
KENTUCKY BLUEGRASS (POA PRATENSIS)
Filed July 7, 1969
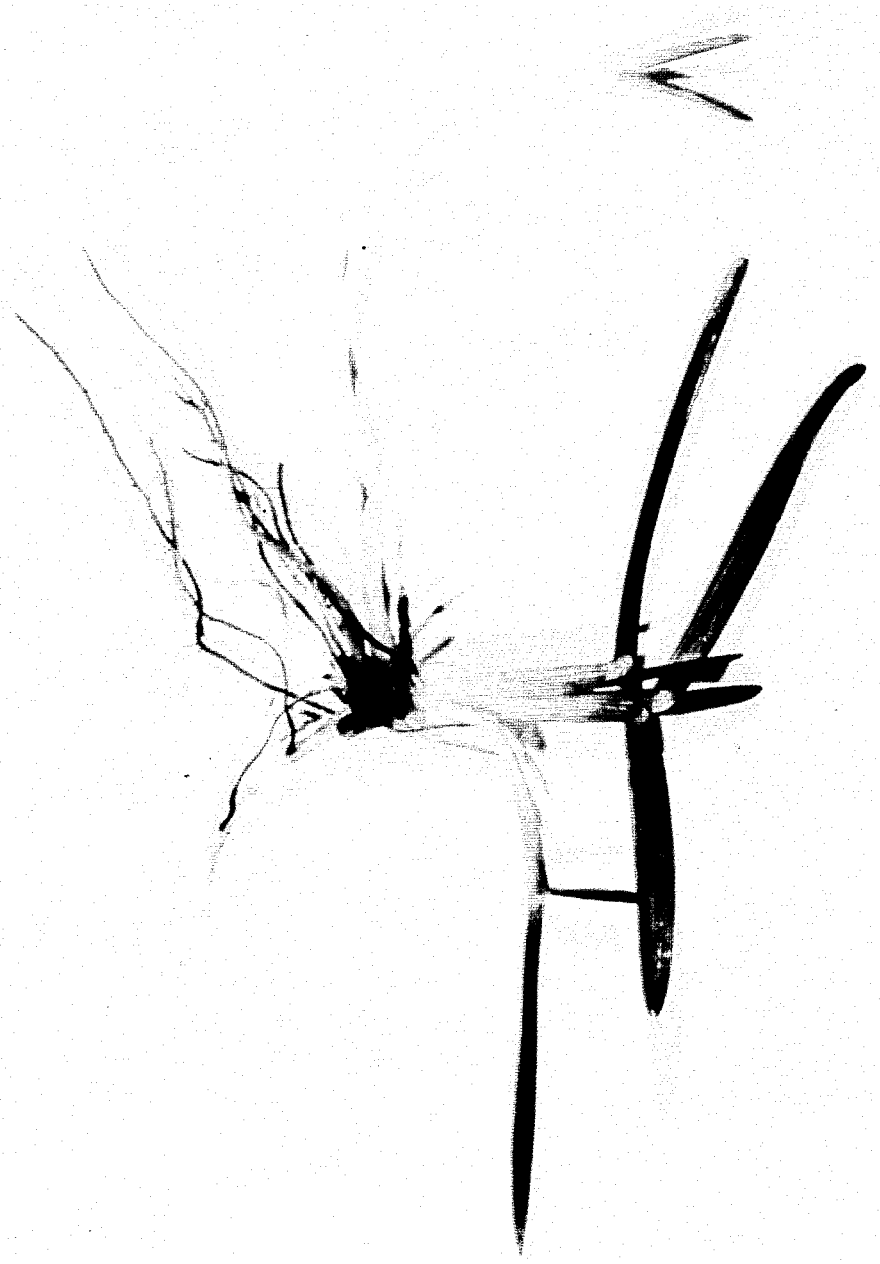
INVENTOR.
WILLIAM H. DANIEL
BY: J. W. Nesbitt
ATTORNEY.

United States Patent Office

Plant Pat. 3,135
Patented Apr. 25, 1972

3,135

KENTUCKY BLUEGRASS (*POA PRATENSIS*)

William H. Daniel, West Lafayette, Ind., assignor to Purdue Research Foundation

Filed July 7, 1969, Ser. No. 839,732
Int. Cl. A01h *5/00*
U.S. Cl. Plt.—88 1 Claim

This invention relates to a new Kentucky bluegrass plant (*Poa pratensis*) which was found by me in the rear lawn of E. Anheuser, Sunset Lane, St. Louis, Mo., in 1952. An area about five feet in diameter was observed to be dark green and weed free, and on later observation retained these desirable characteristics and so sprigs were individually collected, returned to Purdue University, West Lafayette, Ind., and increased and observed since said first observation. The plants were labeled "Anheuser Dwarf" Kentucky bluegrass.

The name was derived from the place the plant was found in combination with the outstanding low (dwarf) growth characteristic of this bluegrass plant as will more fully appear from the data presented herein. Anheuser Dwarf has proven more highly apomictic than Merion Kentucky bluegrass or Windsor as described in U.S. Plant Patent No. 2,364.

Anheuser Dwarf bluegrass embodies all, to a significantly improved extent over other bluegrass, the following qualities and characteristics which are useful and desirable for fine lawns, fairways, tees, cemeteries, and the like:

FEATURE (a) Excellent stripe and flag smut resistance.
(b) Very dark green color, wide leaf.
(c) Excellent powdery mildew resistance.
(d) Improved leafspot resistance.
(e) Improved shade tolerance and low clipping tolerance.
(f) Lower growing and dense—lower seedhead height.
(g) Slower growing upright, but good spread.
(h) Less thatch formation.
(i) Only medium stem rust, but excellent leaf rust resistance.

Comparisons set forth hereafter are to other bluegrasses grown and managed in a similar manner to Dwarf. The environmental conditions are specified whenever deemed relevant. Obviously all varietal comparisons are not to other bluegrasses grown at Purdue under exactly identical conditions, but inventor has a long experience with bluegrasses and has made comparisons with other bluegrasses only where the distinctions are pronounced and not such things as have occurred on a "one time" basis only.

(a) *Excellent resistance to stripe and flag smut*

These diseases (*Ustilago striiformis*) and (*Urocystis agropyri*) develop in susceptible turf after two or more years and are systemic. Severe weakening, thinning and die back results. Merion and Windsor (U.S. Plant Patent No. 2,364) are noted for susceptibility. Resistance permits long term survival as needed in turf. Neither other varieties nor patented clones to date have this resistance, so this is new and unique to Dwarf.

Resistance to Stripe and Flag Smut

| Selection | Age of stand and smutted tillers/sq. ft. | | |
|---|---|---|---|
| | 3 years | 4 years | 5 years |
| Dwarf | 0.1 | 0.3 | 1.1 |
| Pennstar | 0.2 | 0.8 | 4.7 |
| Merion | 7.7 | 41 | [1] 112 |
| Newport | 1.2 | 13 | 37 |

[1] Severe.

Source.—Report of Funk and Engel, Table 3, 1966. "Dwarf showed excellent resistance to stripe smut (*Ustilago striiformis*) in all tests."

(b) *Very dark green color and wide thick leaf*

A distinctive dark green color permits identity in any series of turf plots planted before date of this application. Data from all testing confirms its unique and novel degree of greenness when under good management conditions.

Color Rating for Dates
(10 best to 1 poorest)

| Selections | 1963 | | 1964, | 1963, | 1964, | |
|---|---|---|---|---|---|---|
| | 3/9 | 4/13 | 3/30 | 12/2 | 11/26 | Avg. |
| Dwarf | 9.0 | 6.8 | 7.2 | 7.8 | 8.1 | 7.8 |
| Merion | 5.2 | 4.1 | 5.0 | 1.5 | 5.5 | 4.3 |
| Newport | 8.2 | 2.9 | 4.0 | 6.1 | 5.6 | 5.4 |

Report.—Funk & Engel of New Jersey, 1966. "Dwarf has a very rich, dark green color throughout the growing season." "In turf quality Dwarf showed excellent overall rating in turf quality rating 8.4 (of 10) were Merion was 6.6 and Park was 4.8."

Another study made in 1968 using 3600 unmowed individual plants showed 225 plants of Dwarf had an average rating of 3.3 (where 1 is darkest and 9 is lightest in total field). In leaf width Dwarf is wider than Merion or Newport as indicated.

Rating

| Selection | Color, 1-dark, 9-light | Leaf width, 1 narrow, 9-wide | Growth habit, 1 low | Aggressive spread, 1 most | Density, 1 dense, 9 sparse | Leaf rust, 1 no lesions |
|---|---|---|---|---|---|---|
| Dwarf | 1 | 6 | 5 | 4 | 4 | 8 |
| Merion | 3 | 4 | 3 | 5 | 4 | [1] 9 |
| Newport | 3 | 4 | 3 | 3 | 6 | [2] 1 |

[1] Poorest. [2] Best.

Source.—Melkerson thesis, Table 9, Purdue University, 1963.

(c) *Excellent powdery mildew resistance*

Powdery mildew (*Erysiphe graminis*) is a parasitic disease which weakens and thins turf in moist and shady locations so common to turf usage. (Merion, Windsor, Prato are noted for susceptibility.) Dwarf's excellent resistance to powdery mildew is superior to all varieties mentioned below.

Powdery Mildew Resistance—Field

| Selection | Rating | |
|---|---|---|
| Dwarf | 1 | From Table 8, Melkerson thesis, Purdue, 1963. |
| Merion | 9 | |
| Newport | 2 | |
| Average 28 tested | 3.3 | |

Powdery Mildew Resistance—Greenhouse

| Selection | Powdery mildew | Height, cm. | Planted 11/7/63. |
|---|---|---|---|
| Dwarf | 1 | 13 | Rated 2/19/64. |
| A-10 experimental | 7 | 14 | Purdue data rating: 1=best; 9=least. |
| Cougar | 2 | 14 | |

(d) *Superior leafspot and melting out resistance*

Leafspot shows as lesions on leaves, then entire leaf is killed, then sheaths, crowns and rhizomes are damaged as melting out stages. Long periods of wet, humid, cool to warm weather favor intense damage to susceptible varieties. Organisms of *Helminthosporium vagans, H. giganteum, H. dictyoides* and *H. sativium* may be joined by *Curvularia geniculata* in melting out phases. Merion, Windsor, Prato, Cougar are among those severely damaged by *H. sativium* which builds up in late fall, remains semi-active over winter, and causes much tiller and leaf kill in wet spring. Dwarf has excellent resistance to the *H. sativium.*

*Helminthosporium vagans*—Tolerance

| Selection | Percent turf loss due to leafspot | | | |
|---|---|---|---|---|
| | Spring 1964 | Spring 1965 | Average | Source |
| Dwarf | 4 | 1 | 3 very good | C. R. Funk, R. Engel, Rutgers 1966. |
| Newport | 17 | 27 | 22 | |
| Park | 48 | 65 | 56 | |
| Merion | 5 | 7 | 6 good | |

Leafspot Resistance

| Selection | Infection, percent | Source |
|---|---|---|
| Dwarf | 16 | Letter and report from J. A. Long, O. M. Scott & Co. 11/66. |
| Merion | 30 | |
| Newport | 80 | |
| Park | 87 | |
| Common | 70 | |

Leafspot Resistance Ratings Including *Helminthosporium sativium* Shown by Six Year Old Sod

| Selection | Rating A | Rating B | Source |
|---|---|---|---|
| Dwarf | 1 disease free | 1 | Purdue: 1=best; 9=poorest, 3 replicates, 6 ratings. |
| Merion | 4 leafspot and stripe smut. | 5 | |
| Newport | 6 leafspot and stripe smut. | 7 | |
| Cougar | 8 leafspot and stripe smut. | ---------- | |

A. Field 10A1N planted May '60, 3 replicates (1-best; 9-poorest of existing plots).

B. Field 10A1N planted Sept. '60, 3-replicates (1-best; 9-poorest of existing plots).

Dwarf was free of leafspot in July 1961 in plots of The Lawn Institute (R. W. Schery's letter August 1961) when other experimentals there were heavily infested.

(e) *Improved shade tolerance and low clipping tolerance*

Etiolation, long thin leaves, higher leaf emergence from sheaths, plus weakening by persistent diseases combine to kill turf under shade conditions. Dwarf has survived well in demonstration sodding and plantings in shade. Data support includes study under artificial shade, using 0–100% reduction within greenhouse. Dwarf tolerated 60 and 80% shade better than Windsor, and better than Nortsport (experimental from Sweden). At 30–50% shade Dwarf did not show etiolation, while others did. At 70% shade Dwarf retained thick, dark green, wide angle leaves; while Windsor had thin and yellowish leaves. (Mehringer study Agronomy 597,1967). Uniformity of clipping can indicate uniform health of plant. Data below shows Dwarf maintained leaf health.

Grams Dry Clippings for Measured Interval

| Selection | Time | ½" cut | 1" cut |
|---|---|---|---|
| Dwarf | June 1965 | 43 | 49. |
| | August 1965 | | 45, consistent growth. |
| Merion | June 1965 | 11 | 43. |
| | | | 30, weakened growth. |
| Newport | June 1965 | 22 | 48. |
| | | | 23, weakened growth. |

Source.—Letter and report J. A. Long, O.M. Scott Company, 11/66.

(f) *Low growth, good density and low seedhead height*

When a single tiller (crown) increased for 60 days under uniform outdoor space conditions, then all live leaves were hand removed to give leaf blade comparisons.

Live Leaf Blades (sq./cms.) on All Shoots After 60 Days From Single Crown

| Selections | Clipped at 1.5", cm.² | Unclipped, cm.² | Source |
|---|---|---|---|
| Dwarf | 12 | 29 less to remove | Lobenstein's thesis, page 70, 1964, Purdue University. |
| Merion | 34 | 75 | |
| Newport | 20 | No data | |
| Range of all tested. | 69–12 | 92–29—dwarf was least. | |

An outstanding feature of Dwarf is its adaptation to low mowing, and the dense ground cover maintained when well managed. This is illustrated in data below.

Dense Turf, Percent Cover Under Ample Nitrogen and Low Mowing

| Selections | July | | October | | Source |
|---|---|---|---|---|---|
| | ½", percent | 1", percent | ½", percent | 1", percent | |
| Dwarf | 90 | 95 | 90 | 100 | Report J. A. Long, O. M. Scott Co., 11/21/66. |
| Merion | 90 | 95 | 95 | 100 | |
| Common Ky. | 80 | 95 | 80 | 85 | |

Dwarf (rating 3, excellent) equal to Merion, superior to Newport, Common and Park in turf quality in 1965. Rating took into account density, color, uniformity and absence of disease. Rating 1—best: 9—least.

Dwarf produces low to medium seedheads. This favors later harvest, less pollution in burning of straw fields, and less stemminess in mowed turf areas.

In Indiana test in 1968 among 3600 plants, the range in seedhead height was 6 to 30 inches. Dwarf was 18" in that group.

Maturity of seed is medium to late, which is desirable, as it favors long life of leaves.

Turf growth is low medium when unmowed.

7.3" in 1965, source, Berry, 10B3—page 1.
1.2" in 1968, source, Riordan 10B1—page 8.

Spread is average or slightly less as evidenced by ratings of 6.0 in 1965 (60 plant average) and 5.8 in 1968 (225 plants of 3600) when comparative rating of 1 is most spread, and 9 is least.

Early rhizome and tiller formation—as evidenced by replicated counts on seedlings in greenhouse after 4 months—indicate Dwarf is in upper 50%.

Tillers and Rhizomes Formed by Seedlings

| Selection | Tillers | Rhizomes | Source |
|---|---|---|---|
| Dwarf | 20 | 3 | Purdue: Daniel, March, 1965. |
| Windsor | 12 | 1 | |
| 6 experimentals from Minnesota | 14 | 1 | |
| 15 experimentals from New Jersey | 17 | 3 | |

(g) *Slower growing upright but adequate spread*

Dwarf's low growth habit, with leaves formed close to the soil, permits low mowing heights for special uses, and yet retains density and weed resistance. Tiller counts illustrate this ability.

| Selection | 6/14/67 tillers/2" plug | 6/20/68 crab grass infestation | Source |
|---|---|---|---|
| Dwarf | [1] 58 | [2] 2 | Page 23, book 22, Purdue. |
| 0217 | 39 | [3] 4 | |
| Pennstar | 41 | [3] 3 | |
| Newport | 42 | [3] 5 | |
| Windsor | 35 | [3] 9 | |

[1] Most.
[2] Least.
[3] Infestation preceded by severe *H. sativium* damage.

Dwarf has repeatedly shown healthy leaves so its competition to crabgrass has been outstanding as illustrated above.

Early Spread as Shown by Tillers and Rhizomes

| Selection | 11 weeks | 18 weeks | Source |
|---|---|---|---|
| Dwarf | 2.8 | 11.2 | Greenhouse Melkerson thesis, 1963, Purdue. |
| Merion | 2.1 | 8.8 | |
| Average of 28 selections | 1.7 | 6.1 | |

Average total number of rhizomes developing from single tiller of selected bluegrass clones in 7 growth periods.

| Selections | Length of different tests in— | | | | | | |
|---|---|---|---|---|---|---|---|
| | 180 days | 60 days | 180 days | 120 days | 150 days | 60 days | 90 days |
| Dwarf | 108 | 5.5 | 175 | 56 | 28 | 7 | 10 |
| A-10 (Warren's) | 176 | 6.0 | 256 | 73 | 198 | 7 | 44 |
| Merion | 44 | 0.8 | 76 | 16 | 55 | 11 | 30 |
| K-5-47 (Penna.) | 39 | 3.0 | 78 | 31 | 55 | 8 | 11 |
| Range, all plants: | | | | | | | |
| High | 333 | 6.0 | 256 | 164 | 393 | 18 | 103 |
| Low | 39 | 0.8 | 76 | 16 | 55 | 3 | 10 |

Source.—Lobenstein's thesis, Table 3, Purdue University, 1964.

(h) *Less thatch formation*

Growth of young turf illustrates that Dwarf produces less clippings. Observations of plugs in older turf confirm less thatch. However, it is difficult to accurately measure.

Weight of Green Clippings
(lbs./1,000 sq. ft./month)

| Selection | ½" mowing | 1" mowing | Source |
|---|---|---|---|
| Dwarf | 5 | 27 | Letter and report 11/66, J. A. Long, O. M. Scott Co. |
| Merion | 51 | 41 | |
| Newport | 35 | 39 | |

(i) *Medium rust tolerance*

As identification, tolerance to stem rust, *Pucccinia graminis,* is only medium. Based on 60 plants rust resistance was 1.0 best when most susceptible in field were initially damaged, but six weeks later rating of 5 showed average damage at the time (1—best; 9—worst, Berry, 1965).

| Selection: | Source |
|---|---|
| Dwarf, Merion, Newport | Purdue, 1967, page 23, book 22. |

Leaf rust which may thin in early summer has not been observed on Dwarf.

SUMMARY

Excellent stripe and flag smut (*Ustilago striiformis*), a damaging disease to Windsor, Merion and most varieties, has been widely observed. Leafspot tolerance including *Helminthosphorium vagans, H. sativium* and *H. decloydies* has been repeatedly observed as leaves and stems remain clean. Powdery mildew (*Erysiphe graminis*) resistance in greenhouse and field has been exceptional. On Pennstar powdery mildew is a severe problem.

Dollarspot (*Sclerotina homoeocarpa*) will attach very slowly compared to Merion or Windsor, and only at low nitrogen levels. (This is releated to nitrogen level for all bluegrasses.)

The spread is medium in rate, about equal to that of Windsor, A-10, Merion, Nu-dwarf (U.S. Plant Patent No. 2,513), and Fylking in space plantings. Thatch buildup under good maintenance has been less (although this is difficult to measure).

Dwarf is best adapted to ample fertility. It tolerates close mowing and shade, where its slower growth and disease tolerance permits its superior performance.

The individual plant is comparatively compact. (At Lafayette, Ind., seedheads 16" in height when range was 6–30". In 1970 in seed fields in Washington seedheads averaged 22" to top.) And, with slower growth leaf extension is slow. Rhizomes are large, white, with short internodes, and each terminates with one strong tiller rather than a rosette of new tillers. Dark green color as moved turf usually identifies distinctive type of turf.

Leaves.—Exceptionally wide angle 60–90° from stem to blade. Wide leaf 4–6 cm. (wider than Windsor, Nu-dwarf or Merion). When uncut, as spreading space planting, leaves unmowed were 7.3", and in another test 7.2" (when leaves ranged from 2–20 inches in 3900 plants). Ligule is medium and sheaths may split, so subsequent emerging new leaves are very close to older leaves.

Inflorescence.—Strong individual culms produce open, well-developed panicles of 6–10 cm. in length. Whorls are open giving oblong heads. Seed is heavy, dark brown and matures slowly.

I claim:

1. A new and distinct variety of bluegrass plant, substantially as described and illustrated, and particularly characterized by a low and slow growth habit, dark green color and good disease resistance with good recovery from injury.

No references cited.

ROBERT E. BAGWILL, Primary Examiner